US011857695B2

(12) United States Patent
Awaja et al.

(10) Patent No.: US 11,857,695 B2
(45) Date of Patent: Jan. 2, 2024

(54) ANTI-MICROBIAL COATING FOR OBJECTS SUCH AS PROSTHETIC IMPLANTS

(71) Applicant: National University of Ireland, Galway, Galway (IE)

(72) Inventors: Firas Awaja, Galway (IE); Giorgio Speranza, Madrano (IT)

(73) Assignee: National University of Ireland, Galway, Galway (IE)

( * ) Notice: Subject to any disclaimer, the term of this patent is extended or adjusted under 35 U.S.C. 154(b) by 0 days.

(21) Appl. No.: 17/787,786

(22) PCT Filed: Dec. 16, 2020

(86) PCT No.: PCT/EP2020/086584
§ 371 (c)(1),
(2) Date: Jun. 21, 2022

(87) PCT Pub. No.: WO2021/122854
PCT Pub. Date: Jun. 24, 2021

(65) Prior Publication Data
US 2023/0043372 A1    Feb. 9, 2023

(30) Foreign Application Priority Data

Dec. 20, 2019 (EP) .................................... 19218838

(51) Int. Cl.
A61L 27/30 (2006.01)
A61L 27/06 (2006.01)
A61L 27/54 (2006.01)

(52) U.S. Cl.
CPC ............ A61L 27/303 (2013.01); A61L 27/06 (2013.01); A61L 27/54 (2013.01); *A61L 2300/404* (2013.01); *A61L 2400/18* (2013.01)

(58) Field of Classification Search
CPC .................................................... A61L 27/303
See application file for complete search history.

(56) References Cited

FOREIGN PATENT DOCUMENTS

WO    WO-2010/094212 A1    8/2010

OTHER PUBLICATIONS

Ren et al., Growth and accelerated differentiation of mesenchymal stem cells on graphene-oxide-coated titanate with dexamethasone on surface of titanium implants, 2017, Dental Materials, 33, 525-535 (Year: 2017).*

(Continued)

*Primary Examiner* — Dah-Wei D. Yuan
*Assistant Examiner* — Andrew J Bowman
(74) *Attorney, Agent, or Firm* — Morse, Barnes-Brown & Pendleton, P.C.; Martin Z. Zhang, Esq.

(57) ABSTRACT

A method of providing an anti-microbial coating on an object, comprises the steps of pretreating the object in a first oxygen plasma to graft oxygen-based functional groups on the surface of the object by plasma enhanced chemical vapour deposition, coating the pretreated object with a suspension of particulate graphene oxide to provide a graphene oxide coating on the object, treating the object in a hydrocarbon plasma to deposit an amorphous hydrocarbon film on the graphene oxide coating by plasma enhanced chemical vapour deposition, and treating the object in a second oxygen plasma configured to etch and flatten the coatings on the surface of the object. A prosthetic implant having a metal or metal alloy surface and an anti-microbial coating on all or part of the surface is also described.

13 Claims, 4 Drawing Sheets

(56) References Cited

OTHER PUBLICATIONS

Perreault et al "Antimicrobial Properties of Graphene Oxide Nanosheets: Why Size Matters" ACS Nano vol. 9, pp. 7226-7236, 2015.

Ren et al "Growth and Accelerated Differentiation of Mesenchymal Stem Cells on Graphene-Oxide-Coated Titanate with Dexamethasone on Surface of Titanium Implants" Dental Materials vol. 33, pp. 525-535, 2017.

Vaidulych et al "Deposition of Ag/a-C:H Nanocomposite Films with Ag Surface Enrichment" Plasma Processes and Polymers vol. 14, pp. 1-8, 2017.

* cited by examiner

ANTI-MICROBIAL COATING FOR OBJECTS SUCH AS PROSTHETIC IMPLANTS

CROSS-REFERENCE TO RELATED APPLICATIONS

This application is the National Stage of International Application No. PCT/EP2020/086584, filed on Dec. 16, 2020, which claims priority to EP Application No. 19218838.1, filed on Dec. 20, 2019. The contents of both applications are hereby incorporated by reference in their entirety.

FIELD OF THE INVENTION

The present invention relates to an object having an anti-microbial coating. Also contemplated are methods of forming the anti-microbial coating on the object.

BACKGROUND TO THE INVENTION

Medical implants revolutionize the fields of orthopaedics and surgery by providing solutions to skeletal fractures that were not treated properly otherwise. Medical implants are largely made from Titanium alloys and polymers (such as PEEK). A fundamental requirement for medical implants is to have mechanical properties (such as Young's moduli) similar to that of bone. For this reason, Ti is mixed with other metals to form alloys to achieve the correct value of Young modulus. Among other alloys Ti-6Al-4V is currently one of the most popular alloys for implantation. However, Al and V have been shown to be unsafe, and researchers have suggested other grades of alloys, such as Ti-30Nb-1Fe-1Hf, Ti-6Al-7Nb and Ti-15Sn-4Nb-2Ta-0.2Pd. All these implants materials suffer from poor integration with the human body and require extensive immune suppression process to avoid body rejection. That will escalate bacterial infection and the formation of biofilms which creates further medical complications.

Silver and its derivatives are the most common antibacterial substance that is used currently in medical implants technology. Silver ions perform work by punching holes in bacterial membranes and bind to essential cell components like DNA, preventing the bacteria from performing basic functions. However, the actions of silver is short lived because it depends on the concentration of silver ions. While some bacteria in direct contact with silver ions would be killed, this will not prevent the growth and functioning of bacteria once the ions are depleted.

Perrault F. et al. ("Antimicrobial properties of graphene oxide nanosheets why size matters". ACSNano, (2015), 9, 7226) describes the antimicrobial activity developed by graphene oxide, specifically towards gram negative bacteria *E. Coli*. The paper observes a correlation between the dimension of the graphene oxide patches composing the surface and the antibacterial activity. This is explained as the possible penetration of the edges of the graphene oxide into the cell membrane causing irreversible damage and bacterial death. Possible release of GO flakes from the surface is unwanted. It has consequences on both the dispersion of flakes in the body where the surface is placed and on the stability of the surface on long periods.

Ren N A et al. ("Growth and accelerated differentiation of mesenchymal stem cells on GO coated titanate with dexamethasone on surface of titanium implants". DentMater. (2017), 33, 525) describe depositing a coating made by GO flakes on NaOH treated Ti. The Ti surface was subsequently functionalized by 3-APTES and GO flakes bonded to the functionalized Ti surface. A second coating was obtained by reducing the GO with hydrazine. Both the behavior of Ti+GO and Ti+rGO surface were then treated with dexamethasone (DEX) a corticosteroid generally used in all the anti-inflammatory attributes. It also possesses immunosuppression properties, and it is used as an adjuvant in antibacterial treatments.

Vaidulych M. et al. ("Deposition of Ag/a-C:H nanocomposite films with Ag surface enrichment", Plasma Proc. Polym. (2017), 1600256) describe an amorphous hydrogenated carbon film decorated with Ag nanoparticles to fabricate a surface possessing bactericidal properties. The amorphous CH film is utilized to stabilize the Ag nanoparticles and functions as a neutral matrix in which Ag nanoparticles are embedded. With time Ag ions are released form the surface thus providing bactericidal properties to the surface.

WO 2010-094212 describes a process for functionalization of a Ti, Ti alloys or other materials used on prosthetics to induce antibacterial activity. The process consists in a plasma treatment utilized to deposit films, metal nanoparticles or to graft functional groups. Deposition of film containing metal nanoparticles (e.g. Ag and Cu) is known to provide antibacterial properties. The toxic effect of prolonged release of Ag ions is also well recognised (see for example Wentong Lu et al. (Effect of surface coating on the toxicity of silver nanomaterials on human skin keratinocytes" Chem Phys Lett. 2010 487(1-3) doi:10.1016/j.cplett.2010.01.027), Hadrup et al. ("Toxicity of silver ions, metallic silver, and silver nanoparticle materials after in vivo dermal and mucosal surface exposure: A review". Regulatory Toxicology and Pharmacology Volume 98, October 2018, Pages 257-267) and Zweiker et al. ("Semi-permanent skin staining associated with silver-coated wound dressing Acticoat", Ann Burns Fire Disasters. 2014 Dec. 31; 27(4): 197-200]). The surface also needs the grafting and subsequent release of specific peptides to obtain bactericidal effects. This is a complicated process, and the peptides will degrade over time, It is an object of the invention to overcome at least one of the above-referenced problems.

SUMMARY OF THE INVENTION

The applicant has addressed the problems of the prior art by providing a coating that is stable and robust, does not release toxic free-radical ions over time, and which has a significant anti-bacterial effect against a range of bacteria (Table 1). The coating is prepared by an initial functionalisation of the surface with an oxygen plasma to graft oxygen-based functional groups to the surface to facilitate subsequent coating of the surface with particulate graphene oxide, and then coating the graphene oxide surface with an amorphous hydrocarbon film using a hydrocarbon plasma. The amorphous hydrocarbon film crosslinks and therefore stabilises the graphene oxide flakes on the surface. The final step comprises etching the surface in an oxygen plasma to reduce the surface roughness (FIG. 3 and FIG. 5) which improves the anti-biofilm effect of the treated surface (FIG. 4). The invention thus provides an anti-fouling, anti-microbial and anti-bacterial coating for object such as medical implants to prevent bacterial adhesion while being nontoxic and optionally promoting the growth and integration with bone tissue (osteo-integration), in time-controlled process. The carbon film is designed with precise functionalities that lead to suppression of the bacterial proliferation and growth on a time scale extended to more than 4 weeks, while encouraging the adhesion and growth of bone cells/tissue simultaneously or at a later stage (depending on the type of implants and the patient conditions). Hence the coating is non-toxic and could be alternated between bacteriostatic and bactericidal effects by altering the plasma condition.

In a first aspect, the invention provides a method of providing an anti-microbial coating on an object, comprising the steps of:
pre-treating the object with oxygen plasma to graft oxygen-based functional groups on the surface of the object
providing a graphene oxide coating on the pre-treated object;
depositing an amorphous hydrocarbon coating on the graphene oxide coating; and
treating the object to etch and flatten the coatings.

The anti-microbial coating may be provided on all or part of the surface of the object.

In one embodiment, the pre-treating step comprises treating the object in a hydrocarbon plasma to deposit a stabilising amorphous hydrocarbon film on the graphene oxide coating by plasma enhanced chemical vapour deposition.

In one embodiment the graphene oxide coating is deposited by coating the pre-treated object with a suspension of particulate graphene oxide.

In one embodiment, the amorphous hydrocarbon coating is deposited on the object by treating the object in a hydrocarbon plasma to deposit a stabilising amorphous hydrocarbon film on the graphene oxide coating by plasma enhanced chemical vapour deposition.

In one embodiment, the step of etching and flattening the coatings comprises treating the object in a second oxygen plasma configured to functionalise, etch and flatten the coatings on the surface of the object.

In one embodiment, the object comprises a metal, metal allow, or a polymer. Thus, the object may be formed from, or comprises a surface or part of a surface formed from, a metal or a metal alloy, or a polymer.

In one embodiment, the metal is titanium or a titanium alloy. In one embodiment, the titanium alloy is selected from Ti-6Al-4V, Ti-30Nb-1Fe-1Hf, Ti-6Al-7Nb and Ti-15Sn-4Nb-2Ta-0.2Pd.

In one embodiment, the first oxygen plasma is obtained by feeding the plasma source with oxygen at a flow rate of 10-100, preferably 40-60 sccm, and an RF power of 200-400, preferably 250-350 W. In one embodiment, the first oxygen plasma is obtained by feeding the plasma source with oxygen at a flow rate of 40-60 sccm (ideally about 50 sccm), and an RF power of 250-350 W (ideally about 300 W).

In one embodiment, the object is pre-treated in the first oxygen plasma for a period of 20-40 (ideally about 30) minutes.

In one embodiment, the suspension of particulate graphene oxide has a concentration of about 1-10, 3-5, and ideally about 4, mg/ml.

In one embodiment, the suspension of particulate graphene oxide is obtained by exfoliation of crystalline graphite in strong acid. The Hummer process may be employed to produce particulate graphene oxide (Hummers et al. Journal of American Chemical Society. 80(6): 1339). The exfoliation process of graphite leads to the formation of a population of particulate where the mean flake dimension ranges from few nanometres up to ~30 μm, 95% of the flakes are generally in the form of monolayers. However, differently from the pure ideal graphene, the graphene oxide is strongly oxidized. The chemical composition of GO is typically Carbon: 49-56%, Hydrogen: 0-1%, Nitrogen: 0-1%, Sulfur: 0-2%, Oxygen: 41-50% where about the half of the carbon atoms are typically in an oxidized from. The particulate graphene oxide is generally the form of an aqueous solution at a pH of 2.2 to 2.5. The particulate graphene oxide typically has a concentration of about 3-5 mg/ml, ideally about 4 mg/ml. The suspension is generally drop cast on the medical device.

In one embodiment, the hydrocarbon plasma is obtained by feeding the plasma source with a hydrocarbon at a flow rate of 30-150, 60-100 and ideally about 80 sccm and an RF power of 100-300, 150-250, and ideally about 200, W. In one embodiment, the hydrocarbon plasma is obtained by feeding the plasma source with a hydrocarbon at a flow rate of about 80 sccm and an RF power of about 200 W.

In one embodiment, the object is treated in the hydrocarbon plasma for a period of 10-20, ideally about 15, minutes.

In one embodiment, the second oxygen plasma is obtained by feeding the plasma source with oxygen at a flow rate of 5-50, 10-30, and ideally about 20 sccm and an RF power of 10-200, 50-150, and ideally about 100 W. In one embodiment, the second oxygen plasma is obtained by feeding the plasma source with oxygen at a flow rate of about 20 sccm and an RF power of about 100 W.

In one embodiment, the object is treated in the second oxygen plasma for a period ranging from 1 to 5 minutes depending on the initial surface roughness.

In one embodiment, the graphene oxide coating has a roughness in the micron range.

In one embodiment, the second oxygen plasma treatment is configured to provide a substantially flattened coating comprising in part the amorphous hydrocarbon film coating and in part the graphene oxide coating. Substantially flattened means that the surface roughness of the substantially flattened coating is less than the surface roughness of the coating prior to the second oxygen plasma treatment.

In one embodiment, the object is a prosthetic implant.

The invention also provides an object comprising an anti-microbial coating obtainable by a method of the invention.

The invention also provides an object having an surface and an anti-microbial coating on all or part of the surface, the coating comprising an inner film of grafted oxygen-based functional groups, a coating of graphene oxide adhered to the inner film, and a coating of amorphous hydrocarbon adhered to the graphene oxide coating, optionally in which the coating is etched and flattened.

In one embodiment, the amorphous hydrocarbon coating is optionally discontinuous.

In one embodiment, the amorphous hydrocarbon coating is partially etched away revealing pockets of graphene oxide.?

In one embodiment, the surface of the object is or comprises a metal or metal alloy.

In one embodiment, the surface of the object is or comprises a titanium or titanium alloy.

In one embodiment, the object is a prosthetic implant.

Other aspects and preferred embodiments of the invention are defined and described in the other claims set out below.

BRIEF DESCRIPTION OF THE FIGURES

FIG. 5: Surface roughness comparison between:

Figure 1:
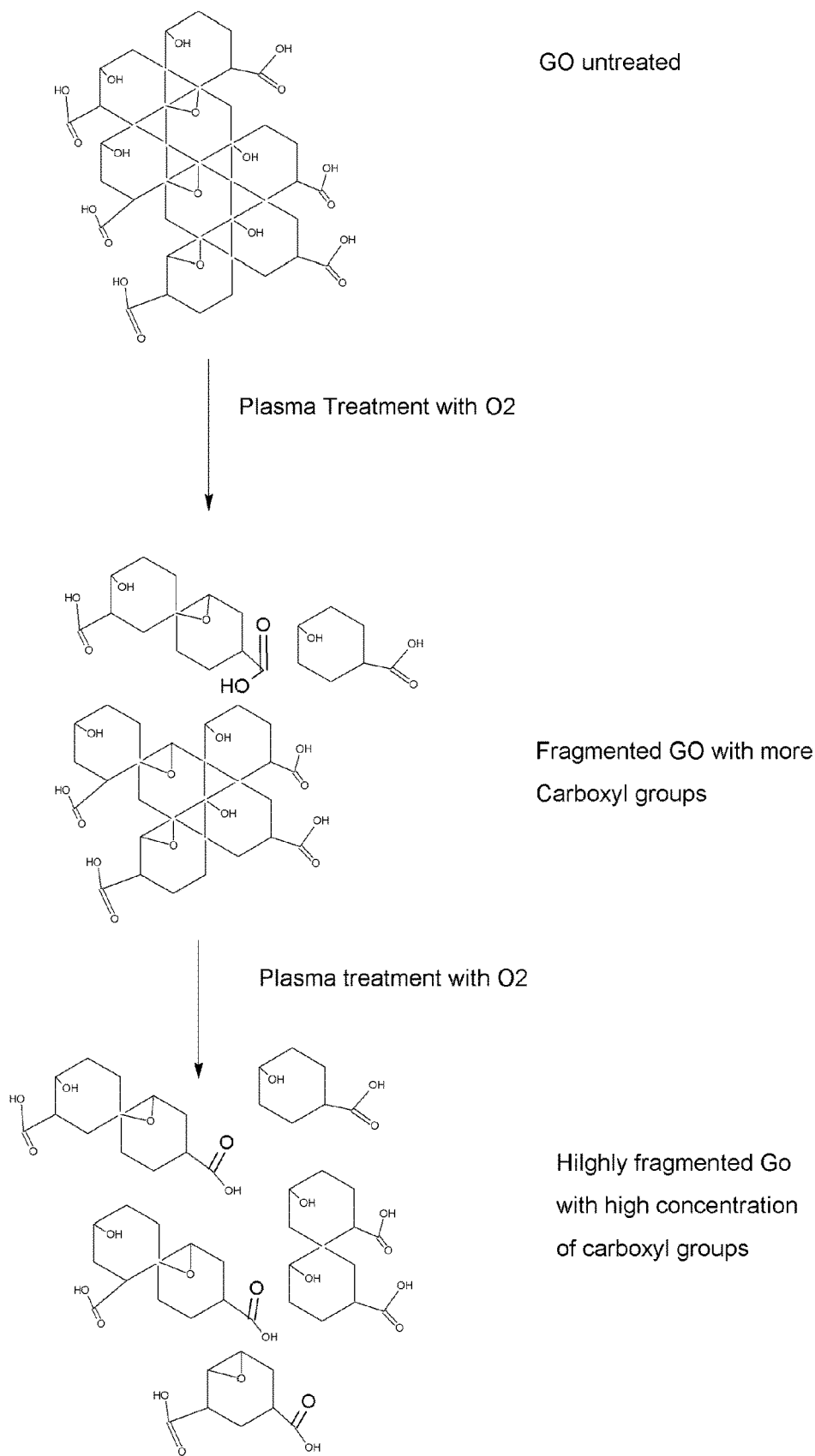
FIG. 1. Schematic diagram showing the fragmentation of GO by plasma treatments to create more carboxyl groups functionalities. The process can be revered using DLC crosslinking to reduce the carboxyl groups functionalities.

Plasma treated MGO coatings of the invention produced with hydrocarbon plasma step and oxygen plasma etching (Plasma MGO coating);

Graphene oxide paper (GO paper);

Reduced graphene oxide coating with no plasma treatment (Reduced GO); and

Modified graphene oxide coating produced with hydrocarbon plasma step and without oxygen plasma etching (Reduced MGO coating).

Plasma MGO coating of the invention exhibits the lowest surface roughness, and smoothest surface, and therefore has better antibacterial properties than the other surfaces.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure. Improvement may be observed in biological/molecular markers, clinical or observational improvements. In a preferred embodiment, the methods of the invention are applicable to humans, large racing animals (horses, camels, dogs), and domestic companion animals (cats and dogs).

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, asses, *kiang* and zebra.

The term "object" as used herein refers to an object with a metal, metal allow or polymer surface that is suitable for treatment with plasma enhanced chemical vapour deposition to graft oxygen-based functional groups on to the surface. The metal may be titanium or a titanium alloy, for example Ti-6Al-4V, Ti-30Nb-1Fe-1Hf, Ti-6Al-7Nb and Ti-15Sn-4Nb-2Ta-0.2Pd. The polymer may be a polymer suitable for use as a prosthetic implant, such as polyether ether ketone (PEEK). In one embodiment, the object is an implantable object, such as a prosthetic implant. Examples of prosthetic devices are hip and knee (and other joint) replacements used in the case of joint degeneration or for various types of arthritis, spinal fusion instruments for treatment of vertebral segments instabilities, and fracture fixation devices such as plates, screws and intramedullary rods.

The term "first oxygen plasma" as used herein typically refers to a RF-generated oxygen plasma generated in a reactor configured to perform low pressure plasma discharges. Typically, the first oxygen plasma is obtained by feeding the plasma source with oxygen at a flow rate of 40-60 sccm and an RF power of 250-350 W. The term "plasma enhanced chemical vapour deposition" refers to a vapor deposition process used to deposit thin films from a gas state (vapor) to a solid state on a substrate. Chemical reactions are involved in the process, which occur after creation of a plasma of the reacting gases.

The term "oxygen-based functional groups" refers to a class of functional groups in which oxygen or molecule containing oxygen is present as the reactive entity. Typically, the oxygen-based functional groups include hydroxyl, carbonyl, or carboxyl molecules. The functional groups are grafted on to the object surface to develop characteristic chemical reactions with other molecules in the environment. As an example, in the case of a titanium surface, the pre-treatment with an oxygen plasma leads to improvement of graphene oxide adhesion to the titanium and prevention of biological fluids permeating the graphene oxide flakes which can lead to their detachment.

The term "suspension of particulate graphene oxide" refers to a suspension of graphene oxide particles having an average dimension of less than 1 μm. The suspension may be prepared by exfoliating crystalline graphite in strong acid to produce a suspension of highly oxidised graphene oxide flakes (Hummer process), and size reduction of the suspension to provide a homogenous suspension of graphene oxide. Size reducing may be performed by sieving the suspension to remove any flakes having a dimension of greater than 1 m, or by sonicating the suspension to size-reduce the flakes. Typically, the suspension has a graphene oxide concentration of about 1-10, 3-5 or about 4, mg/ml.

The term "hydrocarbon plasma" as used herein typically refers to plasma comprising hydrocarbon precursors that is typically generated in a reactor configured to perform low pressure plasma discharges. The hydrocarbon precursors may be various alkanes, for example methane and ethane. Other hydrocarbon precursors that may be employed include benzene and acetylene. The plasma is generally RF-generated. Typically, the hydrocarbon plasma is obtained by feeding the plasma source with a hydrocarbon at a flow rate of 60-100 sccm and an RF power of 150-250 W. The hydrocarbon plasma may include non-hydrocarbon precursors, for example hydrogen to modulate the softness of the DLC coating or $CO_2$ to add oxygen functionalities.

The term "second oxygen plasma" as used herein typically refers to a RF-generated oxygen plasma generated in a reactor configured to perform low pressure plasma discharges. Typically, the second oxygen plasma is obtained by feeding the plasma source with oxygen at a flow rate of 10-30 sccm and an RF power of 50-150 W.

The term "plasma reactor" as used herein typically refers to a plasma reactor configured to generate low pressure plasma discharges. The reactor is typically formed by a load-lock chamber to introduce the medical device into the plasma chamber for treatment. The load lock chamber is typically pumped down from atmospheric pressure down to 10-6 mbar. The evacuation of the load-lock chamber ensures a negligible degree of contaminants to enter in the plasma chamber with the introduction of the objects to be treated. The plasma chamber in one embodiment consists of a stainless teal ellipsoidal chamber with a diameter of ~500 mm to avoid interferences of the chamber walls during the plasma treatment. The plasma chamber is typically equipped with a plasma source which is a commercial COPRA GTE 200 plasma source (from CCR Technology GmbH—Germany). The source is typically equipped with an inner matching network to couple the external RF generator, minimize the reflected RF power and optimize the transfer of the RF power to the plasma. The plasma source is also typically equipped with a magnetic coil. A maximum RF power is transferred to the plasma when the magnetic field is tuned to form a wave resonance (cyclotron resonance) leading to a strong increase of the ionization processes. In this configuration the plasma is generated inside the plasma source and propagated outside through the source output till to the sample surface. The samples are typically then exposed to an after-glow high density plasma but reasonably low power avoiding heat transfer during the depositions. The plasma reactor is typically equipped with a motorized manipulator to ensure a perfect positioning of the medical device under the plasma source.

Figure 3:
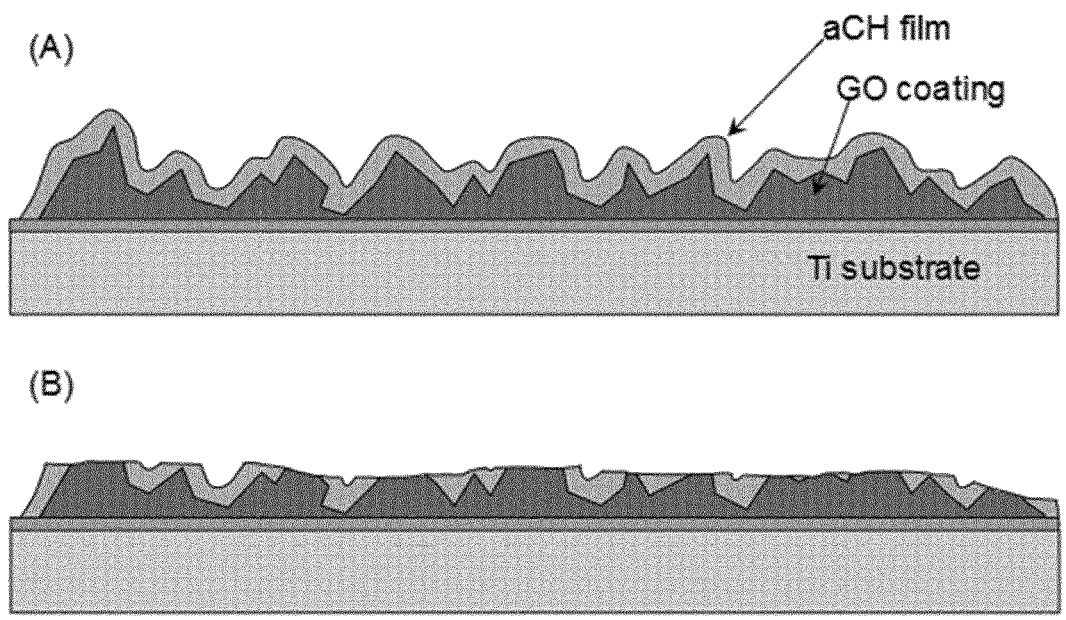
FIG. 3: (A) an aCH film (green) is deposited on the GO coating (grey). (B) the coating after oxygen plasma etching/grafting.
Figure 4:
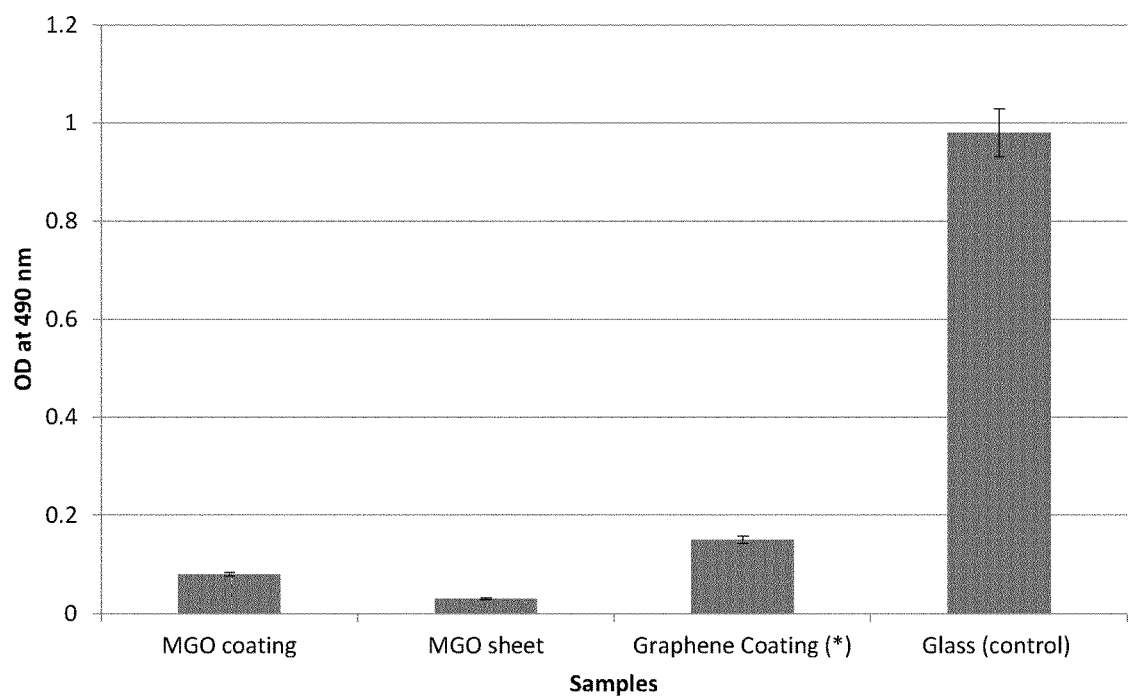
FIG. 4: Biofilm quantification of both modified graphene oxide coated (MGO coating) and free-standing GO (MGO sheet) using crystal violet assay. Pristine graphene (Graphene coating) and uncoated glass were used for reference. Bars are composed of nine measurements including biological (n=3) and technical (n=3) replicates. Biofilm formation was reduced in the MGO coating of the invention compared with both graphene coating and the glass control. The stand-alone MGO sheet exhibits slightly better anti-microbial properties because of geometrical factors and higher cohesion forces. The coatings will have slightly less cohesion as the MGO material must adhere to, and take the shape, of the underlying implant material. The differences is not significant.
Figure 5:
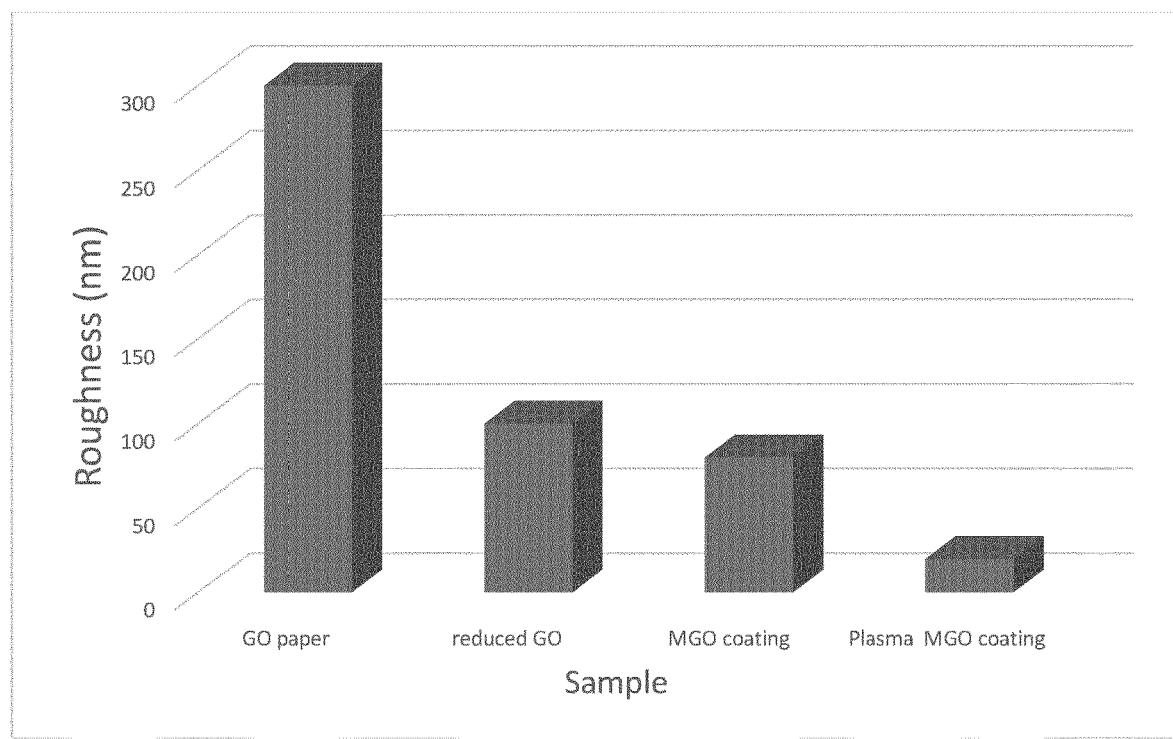

The term "etch and flatten" as used herein refers to process in which the coating on the object is etched to flatten the surface formed by the deposited coating. This is illustrated in FIG. 3. As the graphene oxide coating can be rough, the coating has peaks and troughs of differing height and depths. Etching of the surface involves many of the peaks being etched away, and in one embodiment provides a substantially flattened surface comprising the stabilising amorphous hydrocarbon coating that in parts is etched away revealing pockets of graphene oxide as illustrated in FIG. 3.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

The invention is explained through the synthesis of a multilayered coating for prosthetic implants to avoid bacterial adhesion and proliferation and promote osteo-integration. The deposition of the coating is composed by four steps: 1) preparation of the titanium (or other metal or polymeric based implant) based surface for the deposition of the film; 2) deposition of a first coating composed by GO; 3) deposition of a second coating of amorphous carbon/diamond like carbon with specific crosslinking properties and functional groups density aimed at stabilizing the GO on the prosthetic implant surface, and 4) further plasma treatment with different gas precursors to facilitate targeted surface functionalization. FIG. 1 shows the structure changes in GO coating after plasma treatment (fragmentation) followed by oxygen treatment to increase the concentration of carboxyl group. This procedure will extend the effect of "oxidative stress" that provide free radicals that leads the destruction of bacterial cells. Different treatment could lead to the reduction of carboxyl groups and increase the amorphous carbon content to discourage bacterial adhesion. The methods combined can create areas at the microscale that alternating in action or can be applied at different surfaces depending on the implant type and the required action. Hence. the coatings represent multiple anti-bacterial actions. The cross-linking amorphous carbon layer present bacteriostatic properties while the GO with carboxyl groups represent bactericidal effects.

Carboxyl groups only present at the edges of the graphene oxide sheets. There density depends on the length of these GO layers. Plasma treatment can reduce the length of the GO layers by breaking them into separate smaller fragments then with oxygen plasma, it creates the environment for more carboxyl groups (FIG. 1).

Plasma Reactor

The plasma reactor is generally designed to perform low pressure plasma discharges. The reactor is typically formed by a load-lock chamber to introduce the medical device into the plasma chamber for treatment. The load lock chamber may be pumped down from atmospheric pressure down to 10-6 mbar. The evacuation of the load-lock chamber ensures a negligible degree of contaminants to enter in the plasma chamber with the introduction of the objects to be treated. The plasma chamber may consist of a rather big stainless teal ellipsoidal chamber with a diameter of ~500 mm to avoid interferences of the chamber walls during the plasma treatment. The plasma chamber may be equipped with a plasma source which is a commercial COPRA GTE 200 plasma source (from CCR Technology GmbH—Germany). The source may be equipped with an inner matching network to couple the external RF generator, minimize the reflected RF power and optimizing the transfer of the RF power to the plasma. The plasma source may also be equipped with a magnetic coil. A maximum RF power is generally transferred to the plasma when the magnetic field is tuned to form a wave resonance (cyclotron resonance) leading to a strong increase of the ionization processes. In this configuration the plasma is generated inside the plasma source and propagated outside through the source output till to the sample surface. The samples are generally then exposed to an after-glow high density plasma but reasonably low power avoiding heat transfer during the depositions. Finally the plasma reactor is generally equipped with a motorized manipulator to ensure a perfect positioning of the medical device under the plasma source.

Pretreatment of the Prosthetic Implant Surface

A prosthetic implant under consideration is generally made from metallic alloys based on titanium which continue to be one of the most important components for orthopaedic implants in industry due the high strength, rigidity, fracture toughness and their reliable mechanical performances. However, other type of metals or polymers (PEEK) would also qualify albeit the treatment conditions will slightly vary, accordingly. Prosthetic implants are medical devices used to replace parts of human hard tissue. Examples of prosthetic devices are hip and knee replacements used in the case of joint degeneration or for various types of arthritis, spinal fusion instruments solve vertebral segments instabilities, and fracture fixation devices such as plates, screws and intramedullary rods. Titanium alloys are very versatile materials due to the excellent mechanical properties and the low modulus of elasticity. We initially form a very stable passivating oxide layer on the titanium/implant surface that ensures strong adhesion with the following GO layer. However, alone, this oxide layer provide high biocompatibility and good corrosion resistance. In addition the same oxide layer helps the process of osteo-integration which makes this material an excellent candidate for use in orthopaedics.

The deposition of a graphene oxide on the surface of the titanium alloy was demonstrated to possess bactericidal and bacteriostatic properties depending on the coating process. Pre-treatment of the Ti alloy is a prerequisite to avoid detachment of the GO based coatings. For this purpose, an oxygen plasma treatment is performed in the low pressure plasma reactor.

The plasma pre-treatment is intended to remove all the organic contaminations and graft favourable functional groups to stably bind the GO flakes to the Ti surface. As observed, the Ti surface is formed by Ti oxide which is very stable compound. For this reason the plasma treatment consists of an oxygen plasma obtained by feeding the plasma source with 50 sccm of pure O2 at an RF power of 300 W. These conditions lead to the formation of an oxygen plasma rich in oxygen radicals which are able both to eliminate the organic contaminants form the Ti surface and induce oxygen based functional group grafting on the Ti alloy surface. The treatment was performed for a time of 30 min to optimally functionalize the alloy surface. This also ensures perfect surface homogeneity allowing optimal deposition of the GO film.

Deposition of the GO Layer

After treatment the medical device undergoes a coating with a GO layer. The Graphene Oxide is generally obtained from exfoliation of crystalline graphite through a chemical processing in a strong acid solution (Hummer process—Hummers, William S.; Offeman, Richard E. (Mar. 20, 1958). "Preparation of Graphitic Oxide". Journal of the American Chemical Society. 80 (6): 1339. doi:10.1021/ja01539a017). The exfoliation process leads to a solution of strongly oxidized graphene flakes. Originally the graphene is composed by a single layer of carbon atoms arranged in a hexagonal crystalline lattice. The graphene monolayer is a 2D material characterized by outstanding specific surface. The exfoliation process of graphite leads to the formation of a population of particulate where the mean flake dimension generally ranges from few nanometres up to ~30 µm, 95% of the flakes are in the form of monolayers. However, differently from the pure ideal graphene, the graphene oxide appears to be strongly oxidized. The chemical composition of GO is typically Carbon: 49-56%, Hydrogen: 0-1%, Nitrogen: 0-1%, Sulfur: 0-2%, Oxygen: 41-50% where about the half of the carbon atoms are usually in an oxidized from. The graphene oxide is in the form of an aqueous solution at a pH of 2.2, 2.5 and a concentration of 4 mg/ml. The solution is drop cast on the medical device.

Figure 2:
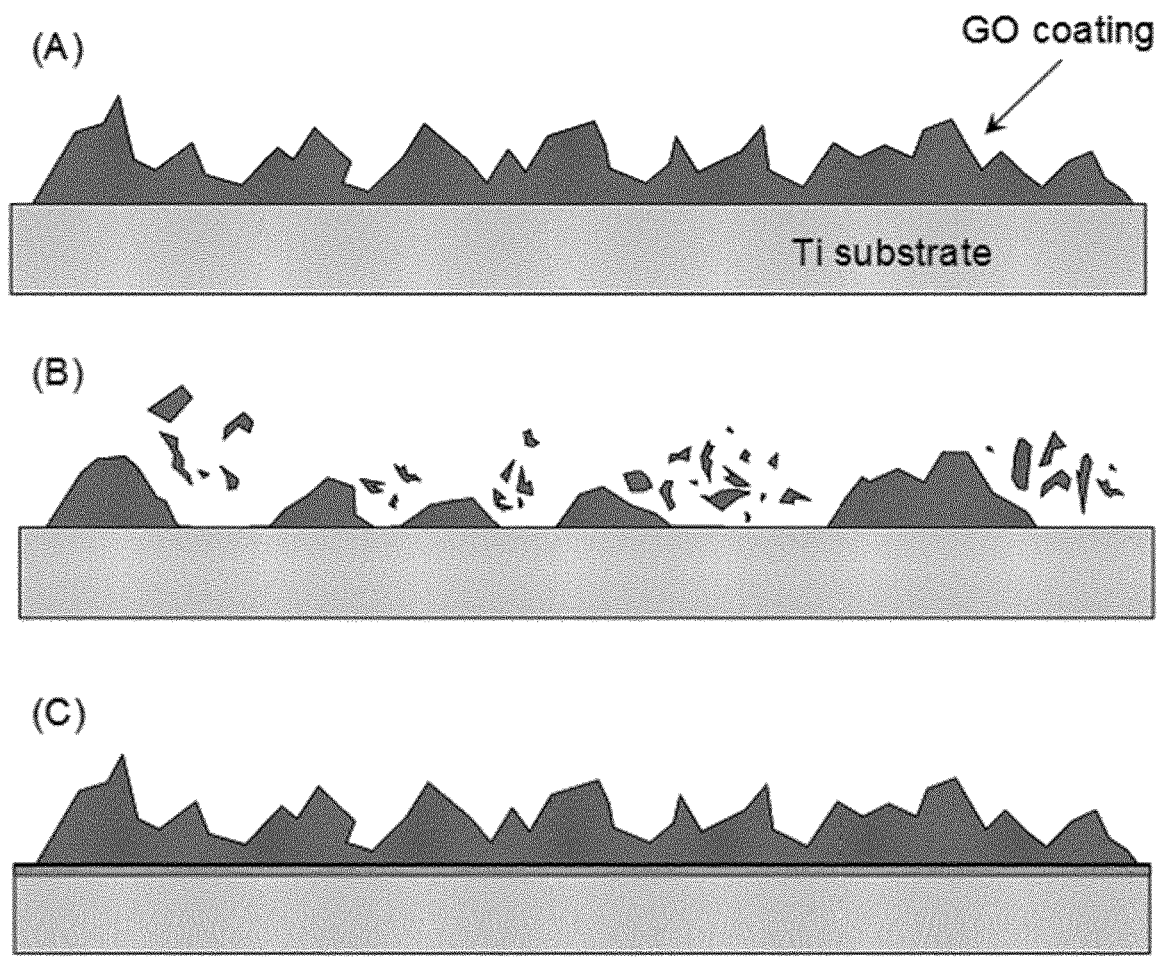
FIG. 2: (A) GO coating of a Ti based surface. Due to the corrosive environment, biological fluids can penetrate at the interface between GO and Ti causing film detachment (B) with release of GO debris. The presence of a Ti pretreatment improves the film adhesion to Ti preventing detachment (C).

Without any surface pre-treatment the GO coating could undergo a detachment from the Ti substrate with release of GO debris in the host biological environment. This case is sketched in FIG. 2. To avoid this undesired event, Ti is pretreated with an oxygen plasma as described above leading to improvement of the GO film adhesion to Ti and preventing biological fluids to permeate the GO flakes leading to their detachment. The GO flakes, undergo screening and sieving process in order to separate the large agglomerations and large particles to keep particles under 1 micron in size.

C-Based Film Deposition and Further Functionalization

The pre-treatment of the Ti substrate induces an interaction between Ti and the first flakes of GO which came into contact with Ti. This treatment, however, has no effect on the topmost layers of the GO coating. To further improve the stability of the GO coating on the Ti alloy, a deposition of an amorphous hydrogenated carbon (aCH) film is made.

The deposition of the film is performed utilizing the plasma reactor described above. The deposition conditions are 80 sccm of CH4 precursor using a RF power of 200 W for a duration of 15 min. The pressure inside the reactor was 0.015 mbar with an ion density of $10^{12}/cm^3$ thanks to the high efficient coupling between the RF excitation power and the plasma. In these conditions the energy of the ionized species impinging the Ti surface is 15 eV while the estimated current density at the Ti surface is 0.35 mA/cm2.

We also observe that the plasma produced by the COPRA is quasi-neutral meaning that it is composed by roughly the same number of ions and electrons. This allows efficient deposition processes even if the conductivity of the substrates is not ensured as in the case of GO deposited Ti surfaces being GO a highly resistive material. After the deposition of the aCH film. The situation is schematically represented in FIG. 3A The aCH coating enables the GO flakes stabilization maintaining a high biocompatibility of the Ti surface. Particularity of this film is the usual absence of specific polarities which make it reject the colonization of micro-organisms such as bacteria with bacteriostatic properties. This is mainly due to the difficulty of bacteria at conditioning the substrate to deposit the protein-based film (the extracellular matrix in the case of cells, the biofilm in the case of bacteria). Since no polar groups are present on the aCH surface, the interaction of this surface with proteins is rather low. To further improve the bactericidal properties of the surface, a surface etching with oxygen is performed.

The oxygen plasma has two main effects: (1) as shown in FIG. 2(B) the oxygen plasma flattens the Ti coated surface. The plasma treatment is carefully adjusted to etch the asperities of the aCH+GO coating. The power and the density of the plasma (around 100 W, 20 sccm O2).

Adjusted to etch part of the topmost part of the deposited coatings. When roughness is present, the plasma etching proceeds from the top of the severities down to the valleys. By carefully controlling the plasma process, we were able to remove part of the aCH+Go coating leading to an overall flattening of the sample surface as shown in FIG. 2B. The flattening effect has an important influence on the bacterial adhesion since rough surfaces encourage the adhesion of the microorganisms to the substrate. On the contrary, flat surfaces render the adhesion process more difficult. As shown in FIG. 2B, part of the aCH film is still present on the sample surface. This aCH film is now creating a network maintaining the GO flakes stabilized on the Ti surface. (2) as a second important effect of the oxygen plasma we obtain the grafting of oxygen based functional groups. It is proven that GO shows a bactericidal activity thanks to the oxidative stress induced by the amount of radicals present on its surface (please see FIG. 1). Oxygen plasma will increase the number of radicals in the exposed GO parts of the coating. Concerning the other parts made of aCH, the plasma will graft the oxygen-based groups leading to an overall anti-bacterial surface.

GO alone, or treated with N2 plasma, is favourable for osteo-integration. Hence an added step for surface functionalization is needed when a double effect (limiting bio films and osteo-integration) is needed. There will be a process of optimization regarding the double effects of the hybrid coatings. Thicker aCH coatings will ensure longer anti-bio film effects while thinner coatings allow for faster exposure of the GO film necessary for osteo-integration.

Biofilm Quantification with Crystal Violet Assay

Crystal violet (CV) assay was used to measure biofilm formation on GO coated/uncoated glass coupons. Coupons with biofilm were washed and transferred to new plates. For fixation of the biofilms, 1 mL 99% methanol was added for 15 minutes, after which supernatants were removed and the plates were air-dried for 45 minutes. Then, 1 mL of a 0.4% (w/v) CV solution (Sigma-Aldrich, 61135-100 G) was added to all wells to stain the biofilms. After 20 minutes, the excess CV was removed by washing the plates under running tap water. Finally, bound CV was released by adding 200 μL of 33% acetic acid (Sigma). The supernatant was added to wells of a 96-well plate and the absorbance was measured at 490 nm. For sterilization, the samples were left 10 minutes on each side under UV lights in biosafety cabinet. Finally, all steps were carried out at room temperature.

Surface Roughness Assay

Surface roughness was measured using an AFM technique. The AFM instrument was Dimension 3100 (Veeco Digital Instruments by Bruker) equipped with a NanoScope IIIa controller and Quadrex signal processor for 16-bit resolution on all 3 axes. The samples were examined under atmospheric pressure and at room temperature with the use of Tapping mode.

Minimum Inhibitory Concentration Assay

MIC is defined as the lowest concentration of an antimicrobial agent that will inhibit the visible growth of a microorganism after overnight incubation. MIC was assessed for five bacterial strains including *Klebsiella pneumoniae, Pseudomonas aeruginosa* and PA-UHG-1, *Staphylococcus epidermidis* and MRSA.

First, for each strain, a 0.5 McFarland standard inoculum, which corresponds approximately 108 CFU/mL was prepared. Then, it was diluted by 100 in sterile MH broth to give an inoculum of approximately 106 CFU/m. This inoculum was used in the 15 minutes following its preparation. In the meantime, serial dilution of liquid GO (0.4 wt %=0.4 g of GO/100 g of solvent) was arranged with the following concentrations: 40 mg/100 g, 20 mg/100 g, 10 mg/100 g, 5 mg/100 g, 2.5 mg/100 g, 1.25 mg/100 g, 0.63 mg/100 g, 0.31 mg/100 g, 0.16 mg/100 g, 0.08 mg/100 g, 0.04 mg/100 g, 0.02 mg/100 g.

Using a sterile Costar U bottom 96-well plate, 10 μL of each GO dilution were loaded in 12 wells, then, 90 μL of the bacterial inoculum were added to the same wells and mixed carefully (approximately 1.105 CFU/well). The experiment was performed in replicate (n=3).

Table 1 shows the MIC results for 5 bacterial strains. (−) sign means no bacterial growth, (+) apparent bacterial growth, (0) means unchanged. This Table shows that the antibacterial process is MGO concentration dependent. But the working concentrations of 2.5 and 1.25 mg MGO/g solvents was taken into consideration when manufacturing the MGO coatings.

TABLE 1

| Bacteria | MGO concentration in solvent (mg of MGO/g of solvent) | | | | | | |
|---|---|---|---|---|---|---|---|
| | 10 | 5 | 2.5 | 1.25 | 0.62 | 0.31 | 0.16 |
| *Klebsiella pneumonia* | 0 | 0 | − | − | + | + | + |
| *Aeruginosa* | | | | | | | |

TABLE 1-continued

| Bacteria | \multicolumn{7}{c}{MGO concentration in solvent (mg of MGO/g of solvent)} | | | | | | |
|---|---|---|---|---|---|---|---|
| | 10 | 5 | 2.5 | 1.25 | 0.62 | 0.31 | 0.16 |
| MRSA | 0 | 0 | – | – | + | + | + |
| Staphylococcus Epidermidis | 0 | 0 | – | – | – | + | + |
| Pseudomonas PA-UHG-1 | 0 | 0 | – | – | – | + | + |
| | 0 | 0 | – | – | + | + | + |

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of providing an anti-microbial coating on an object, comprising the steps of:
   pre-treating the object in a first oxygen plasma to graft oxygen-based functional groups on the surface of the object by plasma enhanced chemical vapour deposition;
   coating the pre-treated object with a suspension of particulate graphene oxide to provide a graphene oxide coating on the object;
   treating the object in a hydrocarbon plasma to deposit an amorphous hydrocarbon film on the graphene oxide coating by plasma enhanced chemical vapour deposition; and
   treating the object in a second oxygen plasma configured to etch and flatten the coatings on the surface of the object.

2. A method according to claim 1, in which the surface of the object comprises a metal or a metal alloy.

3. A method according to claim 1, in which the surface of the object comprises a metal or a metal alloy, and in which the metal is titanium or a titanium alloy.

4. A method according to claim 1, in which the first oxygen plasma is obtained by feeding a plasma source with oxygen at a flow rate of 10-100 sccm and an RF power of 250-350 W.

5. A method according to claim 1, in which the object is pre-treated in the first oxygen plasma for a period of 20-40 minutes.

6. A method according to claim 1, in which the suspension of particulate graphene oxide is obtained by exfoliation of crystalline graphite in strong acid.

7. A method according to claim 1, in which the hydrocarbon plasma is obtained by feeding a plasma source with a hydrocarbon at a flow rate of 60-100 sccm and an RF power of 150-250 W.

8. A method according to claim 1, in which the object is treated in the hydrocarbon plasma for a period of 10-20 minutes.

9. A method according to claim 1, in which the second oxygen plasma is obtained by feeding a plasma source with oxygen at a flow rate of 10-30 sccm and an RF power of 50-150 W.

10. A method according to claim 1, in which the object is treated in the second oxygen plasma for a period ranging from 1 to 5 minutes depending on the initial surface roughness.

11. A method according to claim 1, in which the graphene oxide coating has a roughness in the micron range.

12. A method according to claim 1, in which the second oxygen plasma treatment is configured to provide a substantially flattened surface comprising the amorphous hydrocarbon film coating with pockets of exposed graphene oxide coating.

13. A method according to claim 1, in which the object is a prosthetic implant.

* * * * *